United States Patent
Wiley

(10) Patent No.: US 7,879,830 B2
(45) Date of Patent: Feb. 1, 2011

(54) HORMONE REPLACEMENT COMPOSITION AND METHOD

(76) Inventor: Teresa S. Wiley, 2620 Glendessary La., Santa Barbara, CA (US) 93105

( * ) Notice: Subject to any disclaimer, the term of this patent is extended or adjusted under 35 U.S.C. 154(b) by 1102 days.

(21) Appl. No.: 11/212,001

(22) Filed: Aug. 25, 2005

(65) Prior Publication Data

US 2007/0049567 A1 Mar. 1, 2007

Related U.S. Application Data

(60) Provisional application No. 60/607,143, filed on Sep. 2, 2004.

(51) Int. Cl.
*A61K 31/56* (2006.01)
*A01N 45/00* (2006.01)

(52) U.S. Cl. ............... 514/170; 514/169; 514/178; 514/182

(58) Field of Classification Search ............... 514/170, 514/169, 178, 182
See application file for complete search history.

(56) References Cited

PUBLICATIONS

Andreen et al. European Journal of Endocrinology, 2003. vol. 148, pp. 571-577.*
Suvanto-Luukkonen et al. Acta Obstetricia et Gynecologica Scandinavica. 1998, vol. 77, pp. 758-763.*
"Breast Cancer Prognosis, Treatment and Prevention," Ch. 5, "Inhibition of Cell Growth and Induction of Apoptosis," by Bent Formby & T.S. Wiley, p. 125-147, 2002 Marcel Dekker, Inc.

\* cited by examiner

*Primary Examiner*—Sreeni Padmanabhan
*Assistant Examiner*—Samira Jean-Louis
(74) *Attorney, Agent, or Firm*—Brownstein Hyatt Farber Schreck, LLP

(57) ABSTRACT

Hormone compositions including bioidentical hormones dispersed in a lipid-based cream are provided in syringes for dispensation and self-administration by a user. The compositions, which are topically applied by the user, are percutaneously delivered to the vascular system of the user in accordance with a dosage protocol that causes a rhythmic and cyclic variation in the serum hormone levels that mimics the temporal variation in hormone levels present in the serum of a normal premenopausal woman.

6 Claims, 2 Drawing Sheets

HORMONE REPLACEMENT COMPOSITION AND METHOD

This application claims the benefit of U.S. Provisional Application Ser. No. 60/607,143, filed Sep. 2, 2004.

BACKGROUND OF THE INVENTION

1. Field of the Invention

The present invention relates to hormone replacement therapy (HRT) and, more particularly, to compositions for affecting HRT, a device for dispensing such compositions and a method for self-administering such compositions to the skin of a patient to replicate the temporal variation in corresponding hormone levels observed in the serum of a healthy pre-menopausal woman.

2. Prior Art

Conventional hormone replacement therapy (HRT) for women is almost exclusively administered in flat, static doses of proprietary synthetic drug preparations that mimic the action of the body's sex hormone molecules at some, but not all, receptor sites. Such prior art synthetic drug treatment programs are not truly hormone replacement therapy. Specifically, the widespread use of conjugated equine estrogens (Premarin) and synthetic progesterone (progestins) for hormone replacement therapy, as well as for birth control, is common practice. These regimens have changed over time, but each one has been proven to have serious side effects.

SUMMARY

Recently, the use of "natural" hormones (as distinguished from synthetic hormones) has gained some attention, but such natural hormones are still being administered in inadequate, static doses. The present inventors propose a different method for administering HRT called the Wiley Protocol™. The Wiley Protocol is a method by which women vary their doses of bioidentical hormones over a 28-day cycle. The bioidentical hormones are delivered transcutaneously to a user by the topical administration of a composition comprising appropriate bioidentical hormones disbursed in a lipid-based cream that is applied to the skin. The Wiley Protocol includes a follow-up program in which the serum level of the bioidentical hormones are monitored in the women and the women are advised throughout the program.

The contention, described in detail in the book, authored by one of the present inventors (TSW) entitled: "*Sex, Lies and Menopause*" (Wiley, T. S. et al., Morrow/HarperCollins, N.Y. (2003)) is that women's health issues are paramount and only a regimen of natural bioidentical hormones, applied through the skin and in a cyclical and rhythmic pattern mimicking youthful levels, is a suitable and acceptable treatment for the symptoms of peri-menopause and menopause. The aforesaid contention is based on a thorough review of published scientific research, including the work of the present inventor(s), and on-going in-vitro and clinical studies.

Research conducted by one of the present inventors (TSW) (Formby, B. and Wiley, T. S., "Breast Cancer Cell Growth and Programmed Death by Progesterone", in *Breast Cancer*, A. Pasqualini, Editor, Marche Dekker, NY (2002)) in the use of natural hormones as a cancer-fighting agent, and the conclusion that the onset of the diseases of aging can be tied to the decline of sex hormones led to conceiving the idea that conventional regimens for HRT were inadequate because:

1. The dosing regimens did not mimic the serum levels of young, healthy women.

2. The the administration of flat, static doses did not regulate and modulate the normal cyclical processes in a woman's body.

3. The substitution of non-bioidentical hormones for natural, plant-derived bioidentical hormones only provides a "drug" therapy with hormone-like side effects.

4. The typical delivery system (i.e., oral administration) was inadequate for raising the serum levels of bioidentical hormones to a therapeutically effective level without subsequent adverse side-effects, such as liver disease and skin irritation.

Pioneering physicians and practitioners have agreed to prescribe bioidentical hormones for HRT in accordance with the Wiley Protocol, allowing the present inventors to establish clinical evidence of its efficacy through a broad, three-pronged clinical study. There are at least two thousand women currently taking bioidentical hormones for HRT in accordance with the Wiley Protocol, and possibly many more, with the numbers growing every day. With the drawbacks of current standard of care plainly evident, after the work of the Women's Health Initiative, the millions of women who suffer from these symptoms demand an alternative.

The present invention is directed to bioidentical hormone compositions formulated for topical administration and a method for self-administering the compositions that substantially obviates one or more of the limitations of the related art. To achieve these and other advantages and in accordance with the purpose of the invention, as embodied and broadly described herein, the invention includes a method for dispensing and administering compositions comprising bioidentical hormones in a therapeutically effective regimen. The Wiley Protocol is the result of a combination of original basic scientific research in molecular biology, insight, knowledge and testing.

The Wiley Protocol is a novel method for treating the symptoms of peri-menopause and menopause. The Wiley Protocol provides a method for self-administering bioidentical hormone replacement therapy for women. The method comprises, the steps of:

a. Presenting a first composition comprising estradiol in a pharmacologically acceptable vehicle operable for transdermal delivery of the estradiol by topical administration of the first composition; and presenting a second composition comprising progesterone in a pharmacologically acceptable vehicle operable for transdermal delivery of the progesterone by topical administration of the second composition. The first and second compositions are housed in respective first and second dispensers; then b. Applying the first composition to the woman's skin twice daily over a twenty eight day period, and the second composition for 14 days in a quantity sufficient to replicate the temporal variations in the serum concentration of the estradiol and progesterone in the woman in accordance with FIG. 1.

The features of the invention believed to be novel are set forth with particularity in the appended claims. However the invention itself, both as to organization and method of operation, together with further objects and advantages thereof may be best understood by reference to the following description taken in conjunction with the accompanying drawings.

Figure 1:
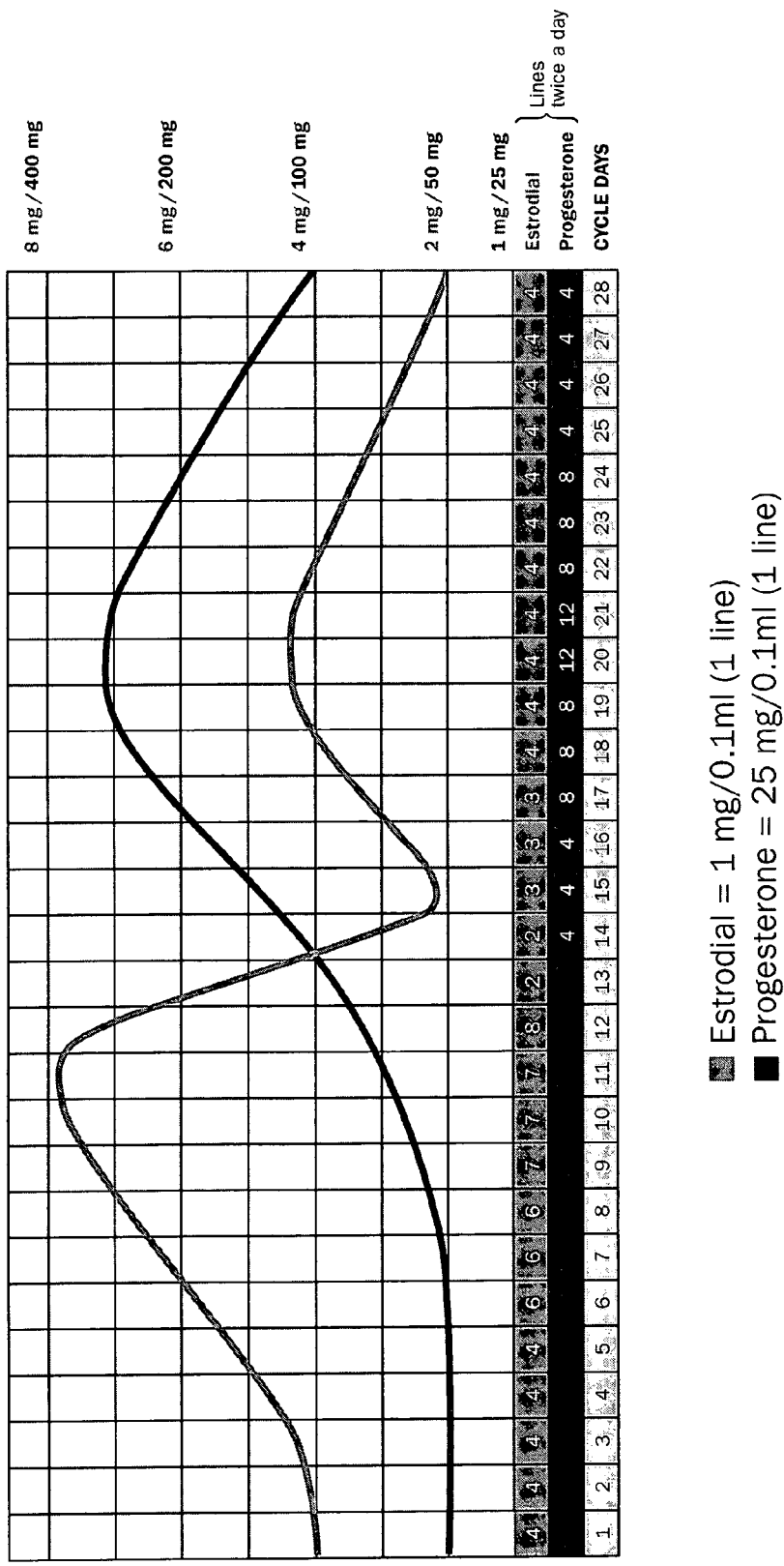
FIG. 1 is a chart of the typical cycles of estrogen and progesterone in a healthy reproductive woman (the curves) and below, the doses by day depicted as "lines" or 0.1 ml demarcations on the syringes.
Figure 2:
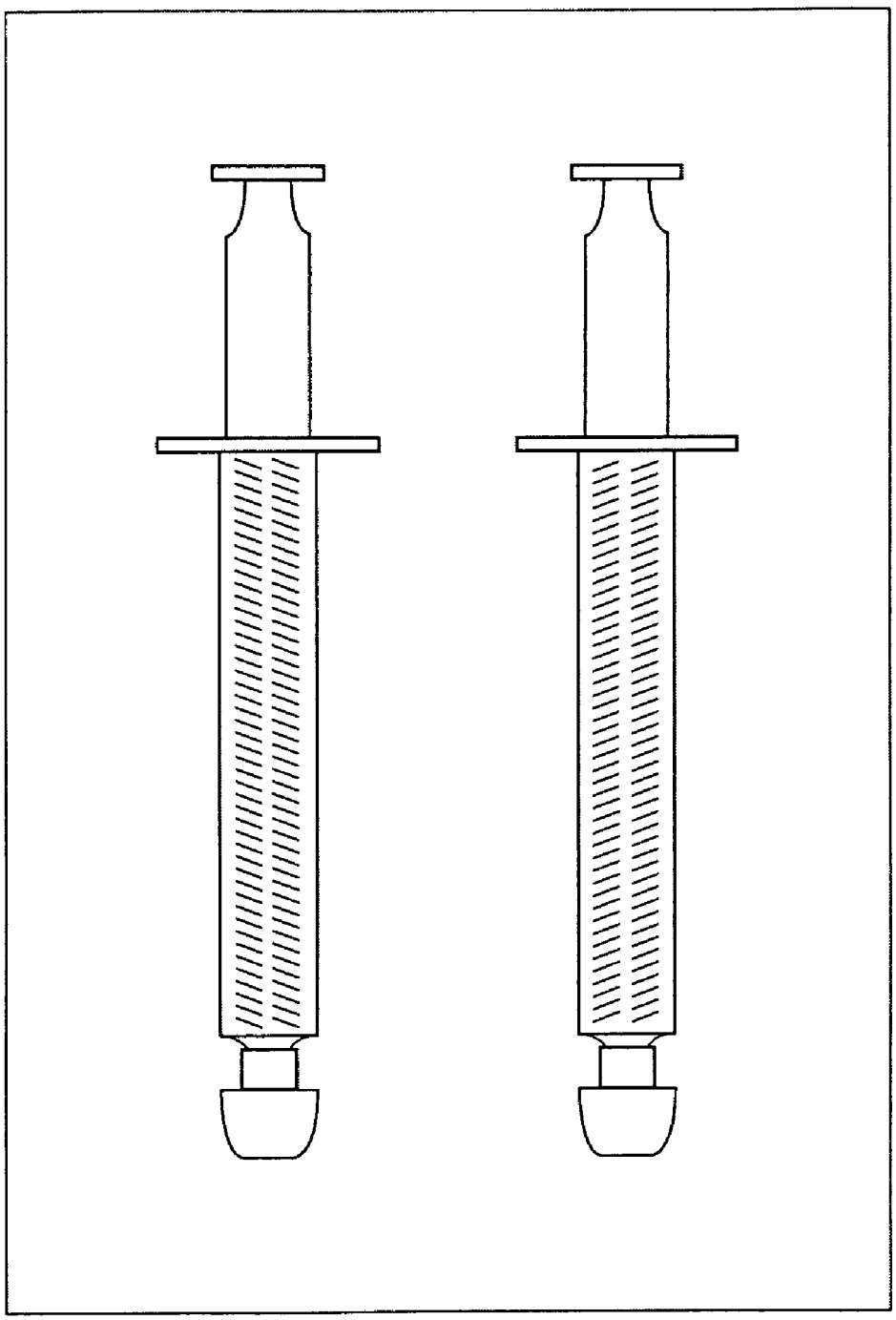
FIG. 2 is a photograph of two 3cc syringes used to apply the hormones transdermally by applying varying doses (measured in "lines" equal to 0.1 ml). The labels read.

Top: Progesterone 25 mg per 0.1 ml Crm
Lot#:040517B
Expiration Date: Nov. 16, 2004
Bottom: Estradiol 1 mg/0.1 ml Cream
Lot#: 040609AA
Exp: Dec. 9, 2004

DESCRIPTION OF THE PREFERRED EMBODIMENTS

Since the Wiley protocol is a more physiologic dosing of bio-identical hormones that may result in greater improvement in quality of life, the protocol is a novel approach to HRT that attempts to mimic a physiologic reproductive hormone cycle in its dose and schedule. Employing only bio-identical estradiol and progesterone in a lipophilic, transdermally applied cream packaged in 3 cc syringes in the concentrations of E2 (estrodiol): 1 mg per 0.1 ml and P4 (progesterone): 25 mg per 0.1 ml, the Wiley Protocol has a standard dosing regimen, which fluctuates over the course of twenty eight days, replicating endogenous production of both hormones occurring in a youthful, premenopausal woman. The Wiley Protocol uses botanical bioidentical hormones administered transdermally in a dose-dependent fashion to restore reproductive levels of estrogen and progesterone in serum. This dosing schedule imitates the normal, healthy output of hormones of a twenty year-old woman. The dose of estradiol, topically administered twice a day, is increased at three-day intervals to a peak on day 12 in the follicular phase and descends to day 14, when progesterone is added. Estradiol continues for the next fourteen days of the luteal phase at mid-range, while progesterone is started on day 14, the dosage increasing to a peak on day 21, and then descending to day 28, when it is halted. The two hormones overlap during the luteal phase. These quantities of estradiol and progesterone are monitored in serum on menstrual cycle days 12 and 21 in all women, regardless of a history of previous hysterectomy, to assure normal physiological levels of estrodiol and progesterone at the peaks of production.

The method for self-administering bioidentical hormone replacement therapy for women may include the first composition being administered to the skin in accordance with the following schedule: 4 mg estradiol twice daily on days 1-5; 6 mg estradiol twice daily on days 6-8; 7 mg estradiol twice daily on days 9-11; 8 mg estradiol twice daily on day 12; 2 mg estradiol twice daily on days 13-14; 3 mg estradiol twice daily on days 15-17; 4 mg estradiol twice daily on days 18-28. The method may also include the second composition being administered to the skin in accordance with the following schedule: 100 mg progesterone twice daily on days 14-15; 200 mg progesterone twice daily on days 16-17; 250 mg progesterone twice daily on days 18-19; 300 mg progesterone twice daily on day 20; 350 mg progesterone twice daily on day 21; 300 mg progesterone twice daily on day 22; 250 mg progesterone twice daily on days 23-24; 200 mg progesterone twice daily on days 25-26; 100 mg progesterone twice daily on days 27-28.

While particular embodiments of the present invention have been illustrated and described, it would be obvious to those skilled in the art that various other changes and modifications can be made without departing from the spirit and scope of the invention. Accordingly, the concentration of bioidentical hormones in the respective vehicles presented herein is exemplary and not to be construed as limiting. It is therefore intended to cover in the appended claims all such changes and modifications that are within the scope of this invention.

I claim:

1. A method for self-administering bioidentical hormone replacement therapy for women, comprising the steps of:
   (a) Presenting a first composition comprising bioidentical estradiol in a pharmacologically acceptable vehicle operable for transdermal delivery of the estradiol by topical administration of the first composition, and a second composition comprising bioidentical progesterone in a pharmacologically acceptable vehicle operable for transdermal delivery of the progesterone by topical administration of the second composition, said first and second compositions being housed in respective first and second dispensers; then
   (b) Applying said first composition to the woman's skin twice daily over a twenty eight day period in a quantity sufficient to replicate the temporal variations in the serum concentration of said estradiol in the woman in accordance with the estradiol curve beginning at cycle day 1 of, wherein the first composition is administered to the skin in accordance with the following schedule: 4 mg estradiol twice daily on days 1-5; 6 mg estradiol twice daily on days 6-8; 7 mg estradiol twice daily on days 9-11; 8 mg estradiol twice daily on day 12; 2 mg estradiol twice daily on days 13-14; 3 mg estradiol twice daily on days 15-17; and approximately 4 mg estradiol twice daily on days 18-28; and
   (c) Applying said second composition to the woman's skin twice daily from the luteal phase to day twenty eight in a quantity sufficient to replicate the temporal variations in the serum concentration of said progesterone in the woman in accordance with the progesterone curve beginning at cycle day 14 of, wherein the second composition is administered to the skin in accordance with the following schedule: 100 mg progesterone twice daily on days 14-15; 200 mg progesterone twice daily on days 16-17; 250 mg progesterone twice daily on days 18-19; 300 mg progesterone twice daily on day 20; 350 mg progesterone twice daily on day 21; 300 mg progesterone twice daily on day 22; 250 mg progesterone twice daily on days 23-24; 200 mg progesterone twice daily on days 25-26; and 100 mg progesterone twice daily on days 27-28.

2. The method for self-administering bioidentical hormone replacement therapy for women in accordance with claim 1 wherein said first composition comprises 1 mg estradiol in 0.1 ml vehicle.

3. The method for self-administering bioidentical hormone replacement therapy for women in accordance with claim 2 wherein said second composition comprises 25 mg progesterone in 0.1 ml vehicle.

4. A method for self-administering bioidentical hormone replacement therapy for women, comprising the steps of:
   (a) presenting a first composition comprising botanical bioidentical estradiol in a pharmacologically acceptable vehicle operable for transdermal delivery of the estradiol by topical administration of the first composition, and a second composition comprising botanical bioidentical progesterone in a pharmacologically acceptable vehicle operable for transdermal delivery of the progesterone by topical administration of the second composition, said first and second compositions being housed in respective first and second dispensers; then (b) applying said first composition to the woman's skin twice daily over a twenty-eight day period so as to restore a reproductive serum level in accordance with the estradiol curve beginning at cycle day 1 in a quantity sufficient to replicate the temporal variations in the serum concentration of said estradiol in the woman;

(c) applying said second composition to the woman's skin twice daily from the luteal phase to day twenty-eight so as to restore a reproductive serum level in accordance with the progesterone curve beginning at cycle day 14 in a quantity sufficient to replicate the temporal variations in the serum concentration of said progesterone in the woman.

5. The method of claim 4, wherein the first composition is administered to the skin in accordance with the following dosing schedule: 4 mg estradiol twice daily on days 1-5; 6 mg estradiol twice daily on days 6-8; 7 mg estradiol twice daily on days 9-11; 8 mg estradiol twice daily on day 12; 2 mg estradiol twice daily on days 13-14; 3 mg estradiol twice daily on days 15-17; 4 mg estradiol twice daily on days 18-28.

6. The method of claim 5, wherein the second composition is administered to the skin in accordance with the following dosing schedule: approximately 100 mg progesterone twice daily on days 14-15; 200 mg progesterone twice daily on days 16-17; 250 mg progesterone twice daily on days 18-19; 300 mg progesterone twice daily on day 20; 350 mg progesterone twice daily on day 21; 300 mg progesterone twice daily on day 22; 250 mg progesterone twice daily on days 23-24; 200 mg progesterone twice daily on days 25-26; 100 mg progesterone twice daily on days 27-28.

* * * * *